(12) United States Patent
Hwang et al.

(10) Patent No.: US 12,344,896 B2
(45) Date of Patent: Jul. 1, 2025

(54) SINGLE NUCLEOTIDE POLYMORPHISM MARKER FOR PRECOCIOUS PUBERTY DIAGNOSIS OR TREATMENT PROGNOSIS PREDICTION, AND USE THEREOF

(71) Applicant: AJOU UNIVERSITY INDUSTRY-ACADEMIC COOPERATION FOUNDATION, Suwon-si (KR)

(72) Inventors: Jin Soon Hwang, Seoul (KR); Seon Yong Jeong, Yongin-si (KR); Hae Sang Lee, Yongin-si (KR); Eun Young Kim, Seoul (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 874 days.

(21) Appl. No.: 17/395,769

(22) Filed: Aug. 6, 2021

(65) Prior Publication Data
US 2021/0395826 A1    Dec. 23, 2021

Related U.S. Application Data

(63) Continuation-in-part of application No. PCT/KR2019/018703, filed on Dec. 30, 2019.

(30) Foreign Application Priority Data

Feb. 8, 2019    (KR) .................. 10-2019-0014993
Apr. 22, 2019    (KR) .................. 10-2019-0046714

(51) Int. Cl.
*C12Q 1/6883* (2018.01)
(52) U.S. Cl.
CPC ..... *C12Q 1/6883* (2013.01); *C12Q 2600/156* (2013.01)
(58) Field of Classification Search
None
See application file for complete search history.

(56) References Cited

U.S. PATENT DOCUMENTS

2014/0378388 A1    12/2014    Morton et al.

FOREIGN PATENT DOCUMENTS

| CN | 108753995 B | 7/2021 |
|---|---|---|
| KR | 10-2014-0072140 | 6/2014 |
| KR | 10-2017-0066079 | 5/2017 |

OTHER PUBLICATIONS

Koh (BioChip J 2018 12(4) 304-308 Pub Dec. 6, 2018).*
Kim (Identification of novel genetic variants associated with precocious puberty by genome wide association analysis in Korean girls, Master's Thesis in Molecular Medicine, Ajou University Feb. 2019).*
Brito (Arch Endocrinol Metab 2016 60/2 pp. 163-173).*
Park, Sung Won, et al. "LIN28B polymorphisms are associated with central precocious puberty and early puberty in girls." *Korean journal of pediatrics* vol. 55 Issue: Oct. 10, 2012 (pp. 388-392).
Rhie, Young-Jun, et al. "KISS1 Gene Polymorphisms in Korean Girls with Central Precocious Puberty." *Journal of Korean medical science* vol. 29 Issue: 8, Jul. 30, 2014; (pp. 1120-1125).
Yi, Bo Ram, et al. "Association between MKRN3 and LIN28B polymorphisms and precocious puberty." *BMC genetics* vol. 19; Article: 47; Jul. 27, 2018; (pp. 1-7).
Luan, Xiaohui, et al. "Association study of the polymorphisms in the KISS1 gene with central precocious puberty in Chinese girls." *European Journal of Endocrinology* vol. 157; Issue:1; Jul. 2007: (pp. 113-118).
김기정.*Identification of novel genetic variants associated with precocious puberty by genome-wide association analysis in Korean girls.* Diss. 2019. (pp. 1-83).
Axiom Precision Medicine Research Array Data Sheet, "Driving Deeper Scientific Insights and Understanding of Individual Genetic Diversity in Global Precision Medicine Screening Research," ThermoFischer Scientific, Jan. 1, 2017, (5 Pages in English).

* cited by examiner

*Primary Examiner* — Amanda Haney
(74) *Attorney, Agent, or Firm* — NSIP Law (57) ABSTRACT

The present invention relates to a single nucleotide polymorphism marker for precocious puberty diagnosis or treatment prognosis prediction for the disease, and a use thereof. In the present invention, the DNA of 700 girl patients of precocious puberty is processed on a microarray chip containing a total of 8,754,887 SNP probes so that SNP genotype data is obtained, and 23 SNPs related to the risk of developing precocious puberty are discovered by means of genome-wide association analysis so that the SNPs can be used for precocious puberty diagnosis or treatment prognosis prediction, early diagnosis of precocious puberty can be conveniently and rapidly carried out, and the prediction of treatment effects and prognosis can be carried, and thus the present invention can be effectively used in a personalized treatment.

4 Claims, 4 Drawing Sheets

SINGLE NUCLEOTIDE POLYMORPHISM MARKER FOR PRECOCIOUS PUBERTY DIAGNOSIS OR TREATMENT PROGNOSIS PREDICTION, AND USE THEREOF

CROSS-REFERENCE TO RELATED APPLICATIONS

This application is a continuation-in-part of an International Application No. PCT/KR2019/018703, filed on Aug. 22, 2017, which claims the benefit under 35 USC 119(a) and 365(b) of Korean Patent Application No. 10-2019-0014993, filed on Feb. 8, 2019 and Korean Patent Application No. 10-2019-0046714, filed on Apr. 22, 2019, in the Korean Intellectual Property Office, the entire disclosures of which are incorporated herein by reference for all purposes.

TECHNICAL FIELD

The present invention relates to a composition for diagnosing precocious puberty or predicting prognosis of treatment for the disease using a single nucleotide polymorphism (SNP) of a gene related to the risk of developing precocious puberty, a method for diagnosing precocious puberty or predicting prognosis of treatment for the disease, and a method for preventing or treating precocious puberty.

BACKGROUND ART

Precocious puberty is a phenomenon in which secondary sexual characteristics appear earlier than 2 standard deviations of the mean value. Generally, it means that secondary sexual characteristics have appeared before the age of 8 years old (breast development before 8 years old, pubic hair development before 9 years old, menarche before 9.5 years old) in girls and before the age of 9 years old in boys. True (central) precocious puberty is a case in which precocious puberty is caused by an increase in the secretion of sex hormones due to early activation of the hypothalamus-pituitary-gonad axis, and pseudoprecocious puberty is a case in which secondary sexual characteristics occur without activation of the hypothalamus-pituitary-gonad axis. In general, it is known that the disease is more commonly occurred 5 to 10 times in girls than in boys.

Several factors are involved in precocious puberty, the first of which is heredity. As a result of investigating the ancestry of 156 patients with precocious puberty in a recent study, it was reported that a case in which parents or siblings had precocious puberty is 27.5%. The second is a westernized diet and an increase in obesity. In a recent study, it was reported that the age of menarche was faster as the degree of obesity increased, and the incidence of precocious puberty was higher in the obese group than in the normal weight group.

If this precocious puberty is not treated, the final height is lost around 12 cm in girls and 20 cm in boys. In addition, in the case of girls, as puberty begins early, menarche is accelerated, and this increases the risk of developing female cancer such as breast cancer, ovarian cancer, and endometrial cancer when they become adults due to early exposure to female hormones. When the age at menarche reaches the age under 12, the risk of breast cancer increases because the hormonal environment according to the regular menstrual cycle begins early and blood estrogen concentration maintains highly throughout the reproductive period from several years after menarche. Recently, the incidence of breast cancer is gradually increasing, which is speculated to be related to the increase in precocious puberty. In addition, many studies have been reported that early menarche increases the incidence of adult obesity and type 2 diabetes.

To diagnose a patient suspected of precocious puberty, the priority is to determine the start time of secondary sexual characteristics (breast development or pubic hair development) through questionnaire and examination. Thereafter, X-rays of the left hand and carpal bones are taken to determine whether the measured bone age is progressed compared to the age. If the secondary sexual characteristics develop rapidly and bone age has been progress, it is essential to perform a gonadotropin-releasing hormone (GnRH) stimulation test to determine whether or not the hypothalamic-pituitary-gonadal axis is activated. After GnRH stimulation, if luteinizing hormone (LH) among puberty hormones is 5 IU/L or more, precocious puberty is diagnosed. However, the GnRH stimulation test, which is the most used for diagnosing precocious puberty until now, has high specificity, but sensitivity is relatively low. It has disadvantages that sensitivity is different depending on the blood luteinizing hormone measurement method, and it has disadvantages that needs to take a blood sample at 4-5 times or more, and that takes a time of 1 hour or more.

Therefore, there is a need to develop a genetic biomarker that can easily and conveniently diagnose or predict precocious puberty. By analyzing genetic biomarkers in connection with clinical information, the prognosis of treatment can be evaluated, and through this, a personalized treatment strategy, such as adjustment of treatment dose and administration cycle, can be established. Since early diagnosis and customized treatment according to the patient's clinical symptoms are particularly important for precocious puberty, a genetic biomarker for customized medical treatment for precocious puberty can be utilized as a very useful diagnostic biomarker.

On the other hand, single nucleotide polymorphisms (SNPs) are the most abundant type of genetic polymorphism in the human genome, and refers to a change in one specific nucleotide sequence on the genome. Genetically, SNPs can cause great differences in individuals depending on their location. For example, when an SNP is present at a protein-encoding position, it may affect the structure of the protein, resulting in a difference in protein function and may be associated with disease. When the SNP is present in a non-coding region that does not encode a protein, that is, a promoter or an intron, it may cause a difference in the expression level of the protein for each, thereby reducing the overall activity of the protein, and also abnormal proteins may be expressed through alternative splicing.

The earlier diagnosis and treatment of precocious puberty, the more effective improvement and treatment of various disorders caused by precocious puberty can be achieved. Therefore, the timing of treatment initiation is very important for precocious puberty. Accordingly, there is a need to develop a biomarker capable of diagnosing precocious puberty and predicting the risk of precocious puberty with high accuracy and sensitivity.

DISCLOSURE

Technical Problem

An object of the present invention is to provide a marker composition for diagnosing precocious puberty or a marker composition for predicting prognosis of treatment for precocious puberty.

Another object of the present invention is to provide a composition for diagnosing precocious puberty or a composition for predicting prognosis of treatment for precocious puberty.

Still another object of the present invention is to provide a kit for diagnosing precocious puberty or a kit for predicting prognosis of treatment for precocious puberty.

Still another object of the present invention is to provide a microarray for diagnosing precocious puberty or a microarray for predicting prognosis of treatment for precocious puberty.

Still another object of the present invention is to provide information on diagnosing precocious puberty or predicting prognosis of treatment for precocious puberty.

Still another object of the present invention is to provide a method for preventing or treating precocious puberty.

Technical Solution

In order to achieve the above object, the present invention provides a marker composition for diagnosing precocious puberty or a marker composition for predicting prognosis of treatment for precocious puberty comprising a polynucleotide consisting of 5-100 consecutive DNA sequences comprising a base at 137937537 position on the human chromosome 5, wherein the base at 137937537 position is C (rs10900855), or a complementary polynucleotide thereof as an active ingredient.

In addition, the present invention provides a composition for diagnosing precocious puberty or predicting prognosis of treatment for precocious puberty, comprising a probe capable of detecting the marker composition or a reagent capable of amplifying the marker composition as an active ingredient.

In addition, the present invention provides a kit for diagnosing precocious puberty or a kit for predicting prognosis of treatment for precocious puberty comprising the composition for diagnosing precocious puberty.

In addition, the present invention provides a microarray for diagnosing precocious puberty or a microarray for predicting prognosis of treatment for precocious puberty comprising the marker composition.

In addition, the present invention provides information on diagnosing precocious puberty or predicting prognosis of treatment for precocious puberty comprising the steps of (a) obtaining DNA or RNA from a sample isolated from a human; (b) amplifying or hybridizing with a probe the polymorphic site of the marker from the DNA or RNA; and (c) identifying the base of the amplified or hybridized polymorphic site.

In addition, the present invention provides a method for preventing or treating precocious puberty including: (a) obtaining DNA or RNA from a sample isolated from a human; (b) amplifying a polynucleotide consisting of 5-100 consecutive DNA sequences comprising C (rs10900855) at 137937537 position on human chromosome from the DNA or RNA, or hybridizing the polynucleotide with a probe; (c) identifying the C of the amplified or hybridized polynucleotide; and (d) administering a pharmaceutical composition including a therapeutically effective amount of a gonadotropin-releasing hormone agonist (GnRHa) to the human.

Advantageous Effects

In the present invention, DNA of 700 girl patients suffering precocious puberty was treated on a microarray chip containing a total of 8,754,887 SNP probes to obtain SNP genotyping data, and 23 SNPs related to the risk of developing precocious puberty were discovered through genome-wide association analysis. Therefore, the SNPs can be used for diagnosing precocious puberty or predicting prognosis of treatment for precocious puberty, and can be usefully utilized for personally customized treatment because it enables simple and quick early diagnosis of precocious puberty and enables prediction on treatment effect and prognosis.

BEST MODE

The inventors of the present invention treated the DNA of 700 girl patients suffering precocious puberty on a microarray chip containing a total of 8,754,887 SNP probes to obtain SNP genotyping data, and discovered 23 SNPs related to the risk of developing precocious puberty through genome-wide association study, thereby completing the present invention.

Accordingly, the present invention provides a marker composition for diagnosing precocious puberty comprising a polynucleotide consisting of 5-100 consecutive DNA sequences comprising a base at 137937537 position on human chromosome 5, wherein the base at 137937537 position is C (rs10900855), or a complementary polynucleotide thereof as an active ingredient.

The composition further comprises one or more polynucleotides selected from the group consisting of a polynucleotide consisting of 5-100 consecutive DNA sequences comprising a base at 30643668 position on human chromosome 11, wherein the base at 30643668 position is T (rs373629); a polynucleotide consisting of 5-100 consecutive DNA sequences comprising a base at 78084567 position on human chromosome 7, wherein the base at 78084567 position is C (rs56252016); a polynucleotide consisting of 5-100 consecutive DNA sequences comprising a base at 130141353 position on human chromosome 9, wherein the base at 130141353 position is A (rs62579679); a polynucleotide consisting of 5-100 consecutive DNA sequences comprising a base at 27973513 position on human chromosome 3, wherein the base at 27973513 position is C (rs4680885); a polynucleotide consisting of 5-100 consecutive DNA sequences comprising a base at 67320971 position on human chromosome 18, wherein the base at 67320971 position is C (rs4891764); a polynucleotide consisting of 5-100 consecutive DNA sequences comprising a base at 188237881 position on human chromosome 3, wherein the base at 188237881 position is G (rs6806402); a polynucleotide consisting of 5-100 consecutive DNA sequences comprising a base at 137554245 position on human chromosome 6, wherein the base at 137554245 position is T (rs17321070); a polynucleotide consisting of 5-100 consecutive DNA sequences comprising a base at 137876920 position on human chromosome 5, wherein the base at 137876920 position is G (rs154069); a polynucleotide consisting of 5-100 consecutive DNA sequences comprising a base at 38920449 position on human chromosome 6, wherein the base at 38920449 position is C (rs35890417); a polynucleotide consisting of 5-100 consecutive DNA sequences comprising a base at 112828038 position on human chromosome 8, wherein the base at 112828038 position is C (rs16882683); a polynucleotide consisting of 5-100 consecutive DNA sequences comprising a base at 134644454 position on human chromosome 7, wherein the base at 134644454 position is A (rs12707194); a polynucleotide consisting of 5-100 consecutive DNA sequences comprising a base at 43645133 position on human chromosome 22, wherein the base at 43645133 position is G (rs11705577); a polynucleotide consisting of 5-100 consecutive DNA sequences comprising a base at 12945963 position on human chromosome 20, wherein the base at 12945963 position is A (rs3903703); a polynucleotide consisting of 5-100 consecutive DNA sequences comprising a base at 2182854 position on human chromosome 5, wherein the base at 2182854 position is T (rs6555069); a polynucleotide consisting of 5-100 consecutive DNA sequences comprising a base at 184087417 position on human chromosome 3, wherein the base at 184087417 position is T (rs9849502); a polynucleotide consisting of 5-100 consecutive DNA sequences comprising a base at 20914430 position on human chromosome 20, wherein the base at 20914430 position is T (rs7267229); a polynucleotide consisting of 5-100 consecutive DNA sequences comprising a base at 16128785 position on human chromosome 12, wherein the base at 16128785 position is G (rs12368628); a polynucleotide consisting of 5-100 consecutive DNA sequences comprising a base at 43431337 position on human chromosome 2, wherein the base at 43431337 position is T (rs72875506); a polynucleotide consisting of 5-100 consecutive DNA sequences comprising a base at 71138478 position on human chromosome 13, wherein the base at 71138478 position is A (rs4083786); a polynucleotide consisting of 5-100 consecutive DNA sequences comprising a base at 2633801 position on human chromosome 25, wherein the base at 2633801 position is C (rs5982579); a polynucleotide consisting of 5-100 consecutive DNA sequences comprising a base at 29812602 position on human chromosome 10, wherein the base at 29812602 position is T (rs7070678); and a polynucleotide consisting of 5-100 consecutive DNA sequences comprising a base at 73531644 position on human chromosome 6, wherein the base at 73531644 position is G (rs10943068), or a complementary polynucleotide thereof.

In the present invention, the term "polymorphism" refers to a case in which two or more alleles exist at a single gene locus, and 'polymorphic site' refers to a gene locus in which the alleles exist. Among polymorphic sites, a single nucleotide that differs from person to person is called 'single nucleotide polymorphism', that is, SNP.

The "allele" refers to several types of a gene present on the same gene locus of a homologous chromosome. Alleles are also used to indicate polymorphism. For example, in the present invention, a single nucleotide polymorphism that can consist of only two alleles is used as a marker. Therefore, the SNPs used in the present invention have two types of biallele.

In the present invention, the term "rs_id" refers to rs-ID, an independent marker given to all SNPs initially registered by the NCBI, which has been accumulating SNP information since 1998. rs_id described in this table means an SNP marker, which is a polymorphic marker in the present invention.

In addition, the present invention provides a composition for diagnosing precocious puberty comprising a probe capable of detecting the marker composition or a reagent capable of amplifying the marker composition as an active ingredient.

The term "probe" used in the present invention refers to a nucleic acid fragment such as RNA or DNA, which can bind to mRNA specifically and consists of several bases for short to several hundred bases for long. Since it is labelled, it can check whether or not a specific mRNA is present, and the expression level of the mRNA. The probe may be manufactured in the form of an oligonucleotide probe, a single strand DNA probe, a double strand DNA probe, an RNA probe, and the like. Suitable probe selection and hybridization conditions may be appropriately selected according to the prior art in the corresponding technical field.

The primer used for amplification of the polymorphic marker refers to a single-stranded oligonucleotide that can serve as a starting point for template-directed DNA synthesis prepared under suitable conditions in an appropriate buffer (e.g., 4 different nucleoside triphosphates and a polymerization agent such as DNA, RNA polymerase or reverse transcriptase) and under appropriate temperature. The appropriate length of the primer may vary depending on the intended use, but is usually 15 to 30 nucleotides. Short primer molecules generally require lower temperatures to form stable hybrids with the template. The primer sequence need not be completely complementary to the template, but must be sufficiently complementary to hybridize to the template.

The "primer" is a base sequence having a short free 3' hydroxyl group. It means a short sequence that can form a base pair with a complementary template and serves as a starting point for copying template strand. The primer is capable of initiating DNA synthesis in the presence of reagents for polymerization (i.e., DNA polymerase or reverse transcriptase) and four different nucleoside triphosphates in appropriate buffers and temperatures.

The length of the sense and antisense primers may be modified based on known in the art. The probes or primers in the present invention may be chemically synthesized using the phosphoramidite solid-phase method or other well-known methods. Such nucleic acid sequences may also be modified using a number of means known in the art. Non-limiting examples of such modifications include methylation, "capping", substitution of one or more homologs of natural nucleotides, and modifications between nucleotides, such as uncharged linkages (e.g., methyl phosphonates, phosphotriesters, phosphoroamidates, carbamates, etc.) or charged linkages (e.g., phosphorothioates, phosphorodithioates, etc.).

The present invention also provides a kit for diagnosing precocious puberty comprising the composition for the diagnosing precocious puberty.

The kit may be a DNA chip kit or an RT-PCR kit, but is not limited thereto.

The kit can diagnose the type by confirming through amplifying the SNP polymorphic marker, which is a diagnostic marker for precocious puberty, or by determining the expression level of the SNP polymorphic marker at the level of DNA or mRNA. As a specific example, the kit for measuring the mRNA expression level of the marker for diagnosing precocious puberty in the present invention may be a kit including essential elements necessary for performing RT-PCR. The RT-PCR kit may include, in addition to each pair of primers specific for the gene of a diagnostic marker for precocious puberty, a test tube or other suitable container, a reaction buffer (with varying pH and magnesium concentrations), deoxynucleotides (dNTPs), enzymes such as Taq-polymerase and reverse transcriptase, DNase, RNAse inhibitors, DEPCwater, sterile water, and the like. It may also include a pair of primers specific for a gene used as a quantitative control. Also preferably, the kit in the present invention may be a kit for diagnosing precocious puberty including essential elements necessary for performing a DNA chip. A DNA chip kit is a generally flat solid support plate, and typically a glass surface no larger than a microscope slide in which nucleic acid species are attached in a gridded array. It is a tool that allows for a large-scale parallel analysis, in which the nucleic acids are uniformly arranged on the chip surface, so that multiple hybridization reactions between the nucleic acids on the DNA chip and the complementary nucleic acids contained in the solution treated on the chip surface.

In addition, the present invention provides a microarray for diagnosing precocious puberty comprising the marker composition.

The microarray in the present invention may include DNA or RNA polynucleotides. The microarray consists of a conventional microarray except that the polynucleotide in the present invention is included as the probe polynucleotide. Methods for preparing microarrays by immobilizing probe polynucleotides on a surface are well known in the art. The probe polynucleotide refers to a hybridizable polynucleotide, and refers to an oligonucleotide capable of sequence-specific binding to a complementary strand of nucleic acids. The probe in the present invention is an allele-specific probe. A polymorphic site exists in nucleic acid fragments derived from two members of the same species, so that it hybridizes to a DNA fragment derived from one member but does not hybridize to a fragment derived from another member. In this case, the hybridization conditions must be sufficiently stringent to hybridize only one of the alleles by showing a significant difference in the hybridization intensity between alleles. This can lead to good hybridization differences between different allelic forms. The diagnostic methods may include detection methods based on hybridization of nucleic acids, such as Southern blotting, and may be provided in a form previously bound to a surface of a DNA chip in a method using a DNA chip. The hybridization may be usually performed under stringent conditions, for example, a salt concentration of 1 M or less, and a temperature of 25° C. or more.

In addition, the present invention provides a method for providing information on diagnosing precocious puberty comprising the steps of (a) obtaining DNA or RNA from a sample isolated from a human; (b) amplifying the polymorphic site of the marker from the DNA or RNA, or hybridizing it with a probe; and (c) identifying the base of the amplified or hybridized polymorphic site.

The DNA or RNA may be isolated from all cells such as blood, skin cells, mucosal cells, and hair of a subject. A method for extracting DNA or RNA from the cells is not particularly limited, and the prior art in the corresponding technical field or a commercially available DNA or RNA extraction kit may be used.

Any method known to those skilled in the art may be used for the step (b) of amplifying the polymorphic site of the single nucleotide polymorphism marker or hybridizing it with a probe. For example, it can be obtained by amplifying a target nucleic acid through PCR and purifying it. Others including ligase chain reaction (LCR) (Wu and Wallace, Genomics 4, 560 (1989), Landegren et al., Science 241, 1077 (1988)), transcription amplification (Kwoh et al., Proc. Natl. Acad. Sci. USA 86, 1173 (1989)), self-sustained sequence replication (Guatelli et al., Proc. Natl. Acad. Sci. USA 87, 1874 (1990)) and nucleic acid sequence based amplification (NASBA) can be used.

Identifying the base of the polymorphic site in step (c) includes sequencing analysis, hybridization by microarray, allele specific PCR, dynamic allele specific hybridization (DASH), PCR Extension analysis, SSCP, PCR-RFLP analysis or TaqMan technique, SNPlex platform (Applied Biosystems), mass spectrometry (e.g., Sequenom's MassARRAY system), mini-sequencing method, Bio-Plex system (BioRad), CEQ and SNPstream systems (Beckman), Molecular Inversion Probe array technologies (e.g., Affymetrix GeneChip), and BeadArray Technologies (e.g., Illumina GoldenGate and Infinium assays), but is not limited thereto. One or more alleles in polymorphic markers may be identified, including microsatellites, SNPs, or other types of polymorphic markers, by the above methods or other methods available to those skilled in the art. Determination of the base of such a polymorphic site may be preferably performed through an SNP chip.

In addition, in the step of identifying the genotype, gene sequence analysis may be performed. Sequence analysis may be used any method known in the art, and specifically, but not limited thereto, may be used an automatic sequencing analyzer, or may be used any one or more selected from known methods such as pyrosequencing, PCR-RFLP (restriction fragment length polymorphism) method, PCRSSCP (single strand conformation polymorphism) method, PCR-SSO (specific sequence oligonucleotide) method, ASO (allele specific oligonucleotide) hybridization method combining PCR-SSO method and dot hybridization method, TaqMan-PCR method, MALDI-TOF/MS method, RCA (rolling circle amplification) method, HRM (high resolution melting) method, primer extension method, Southern blot hybridization method, dot hybridization method, and the like.

In addition, the present invention provides a marker composition for predicting the prognosis of treatment for precocious puberty comprising a polynucleotide consisting of 5-100 consecutive DNA sequences comprising a base at 137937537 position on human chromosome 5, wherein the base at 137937537 position is C (rs10900855), or a complementary polynucleotide thereof as an active ingredient.

The composition further comprises one or more selected from the group consisting of a polynucleotide consisting of 5-100 consecutive DNA sequences comprising a base at 30643668 position on human chromosome 11, wherein the base at 30643668 position is T (rs373629); a polynucleotide consisting of 5-100 consecutive DNA sequences comprising a base at 78084567 position on human chromosome 7, wherein the base at 78084567 position is C (rs56252016); a polynucleotide consisting of 5-100 consecutive DNA sequences comprising a base at 130141353 position on human chromosome 9, wherein the base at 130141353 position is A (rs62579679); a polynucleotide consisting of 5-100 consecutive DNA sequences comprising a base at 27973513 position on human chromosome 3, wherein the base at 27973513 position is C (rs4680885); a polynucleotide consisting of 5-100 consecutive DNA sequences comprising a base at 67320971 position on human chromosome 18, wherein the base at 67320971 position is C (rs4891764); a polynucleotide consisting of 5-100 consecutive DNA sequences comprising a base at 188237881 position on human chromosome 3, wherein the base at 188237881 position is G (rs6806402); a polynucleotide consisting of 5-100 consecutive DNA sequences comprising a base at 137554245 position on human chromosome 6, wherein the base at 137554245 position is T (rs17321070); a polynucleotide consisting of 5-100 consecutive DNA sequences comprising a base at 137876920 position on human chromosome 5, wherein the base at 137876920 position is G (rs154069); a polynucleotide consisting of 5-100 consecutive DNA sequences comprising a base at 38920449 position on human chromosome 6, wherein the base at 38920449 position is C (rs35890417); a polynucleotide consisting of 5-100 consecutive DNA sequences comprising a base at 112828038 position on human chromosome 8, wherein the base at 112828038 position is C (rs16882683); a polynucleotide consisting of 5-100 consecutive DNA sequences comprising a base at 134644454 position on human chromosome 7, wherein the base at 134644454 position is A (rs12707194); a polynucleotide consisting of 5-100 consecutive DNA sequences comprising a base at 43645133 position on human chromosome 22, wherein the base at 43645133 position is G (rs11705577); a polynucleotide consisting of 5-100 consecutive DNA sequences comprising a base at 12945963 position on human chromosome 20, wherein the base at 12945963 position is A (rs3903703); a polynucleotide consisting of 5-100 consecutive DNA sequences comprising a base at 2182854 position on human chromosome 5, wherein the base at 2182854 position is T (rs6555069); a polynucleotide consisting of 5-100 consecutive DNA sequences comprising a base at 184087417 position on human chromosome 3, wherein the base at 184087417 position is T (rs9849502); a polynucleotide consisting of 5-100 consecutive DNA sequences comprising a base at 20914430 position on human chromosome 20, wherein the base at 20914430 position is T (rs7267229); a polynucleotide consisting of 5-100 consecutive DNA sequences comprising a base at 16128785 position on human chromosome 12, wherein the base at 16128785 position of is G (rs12368628); a polynucleotide consisting of 5-100 consecutive DNA sequences comprising a base at 43431337 position on human chromosome 2, wherein the base at 43431337 position is T (rs72875506); a polynucleotide consisting of 5-100 consecutive DNA sequences comprising a base at 71138478 position on human chromosome 13, wherein the base at 71138478 position is A (rs4083786); a polynucleotide consisting of 5-100 consecutive DNA sequences comprising a base at 2633801 position on human chromosome 25, wherein the base at 2633801 position is C (rs5982579); a polynucleotide consisting of 5-100 consecutive DNA sequences comprising a base at 29812602 position on human chromosome 10, wherein the base at 29812602 position is T (rs7070678); and a polynucleotide consisting of 5-100 consecutive DNA sequences comprising a base at 73531644 position on human chromosome 6, wherein the base at 73531644 position is G (rs10943068), or a complementary polynucleotide thereof.

In addition, the present invention provides a composition for predicting prognosis of treatment for precocious puberty comprising a probe capable of detecting the marker composition or an agent capable of amplifying the marker composition as an active ingredient.

In addition, the present invention provides a kit for predicting prognosis of treatment for precocious puberty comprising the composition for predicting prognosis of treatment for precocious puberty.

The kit may be a DNA chip kit or an RT-PCR kit, but is not limited thereto.

In addition, the present invention provides a microarray for predicting the prognosis of treatment for precocious puberty comprising the marker composition.

In addition, the present invention provides a method for providing information on predicting prognosis of treatment for precocious puberty comprising the steps of (a) obtaining DNA or RNA from a sample isolated from a human; (b) amplifying the polymorphic site of the marker from the DNA or RNA, or hybridizing it with a probe; and (c) identifying the base of the amplified or hybridized polymorphic site.

In addition, the present invention provides a method for preventing or treating precocious puberty including: (a) obtaining DNA or RNA from a sample isolated from a human; (b) amplifying a polynucleotide consisting of 5-100 consecutive DNA sequences comprising C (rs10900855) at 137937537 position on human chromosome from the DNA or RNA, or hybridizing the polynucleotide with a probe; (c) identifying the C of the amplified or hybridized polynucleotide; and (d) administering a pharmaceutical composition including a therapeutically effective amount of a gonadotropin-releasing hormone agonist (GnRHa) to the human.

As used herein, "prevention" or "preventing" refers to any action of inhibiting or delaying the onset of precocious puberty by administrating the pharmaceutical composition including a therapeutically effective amount of a gonadotropin-releasing hormone agonist (GnRHa) to the human. In addition, it includes treatment of a human with remission of the precocious puberty for the prophylaxis and the prevention of recurrence.

As used herein, "treatment" or "treating" refers to any action that improves or beneficially alters the condition, such as alleviating, reducing, or eliminating the onset of precocious puberty by administrating the pharmaceutical composition according to the present invention.

As used herein, "pharmaceutical composition" means a composition administered for a specific purpose, and for the purposes of the present invention, it refers to be administered to prevent or treat precocious puberty.

The pharmaceutical composition for preventing or treating precocious puberty according to the present invention may include a therapeutically effective amount of a gonadotropin-releasing hormone agonist (GnRHa).

Furthermore, the GnRHa may be selected from the group consisting of leuprolide, triptorelin, and salts thereof. Specifically, the GnRHa may be leuprolide acetate or triptorelin acetate.

As used herein, the term "therapeutically effective amount" refers to an amount sufficient to treat precocious puberty at a reasonable benefit/risk ratio applicable to medical treatment and does not cause side effects, and the effective dose level can be determined according to factors including the patient's health status, specific type of disease, severity of disease, activity of the drug, sensitivity to the drug, method of administration, time of administration, route of administration and rate of excretion, duration of treatment, drugs used in combination or concurrently, and other factor well known in the medical field.

The pharmaceutical composition may be administered intravenously, intraarterially, intraperitoneally, intramuscularly, intrasternally, transdermally, nasally, inhaled, topically, rectally, orally, intraocularlly or intradermally to a human in the conventional manner.

The preferred dosage of the pharmaceutical composition may vary depending on the condition and weight of the human, the specific type and extent of the disease, the drug form, the route of administration, and the duration, and may be appropriately selected by those skilled in the art. The pharmaceutical composition may be administered once a day or divided into several times, and the scope of the invention is not limited thereto.

MODES FOR CARRYING OUT INVENTION

Hereinafter, the present invention will be described in more detail through examples. These examples are only for illustrating the present invention in more detail, and it will be apparent to those skilled in the art that the scope of the present invention is not limited by these examples according to the gist of the present invention.

Example 1: Sample Preparation

Consent to the participation and information on the health and puberty status of the participants were provided from Korean little girls who came to the hospital with suspected symptoms of precocious puberty and the parents of the girls.

When secondary sexual characteristics such as breast development, pubic hair development, and menarche appeared before the age of 8 in the little girls, a gonadotropin-releasing hormone (GnRH) stimulation test was performed. Precocious puberty was diagnosed when the highest level of luteinizing hormone (LH) was measured to be 5 IU/L or more, and bone age was higher than the inverse age.

Blood from 700 girl patients with precocious puberty and 300 normal little girls were collected and genomic DNAs were extracted with the Exgene™ Blood Kit (GeneAll, Seoul, Korea). After then, the DNA quality and quantity were determined by the UV absorbance values of 260/280 and 260/230. In addition, the quality of all DNA samples was additionally confirmed using agarose gel electrophoresis.

Figure 1:
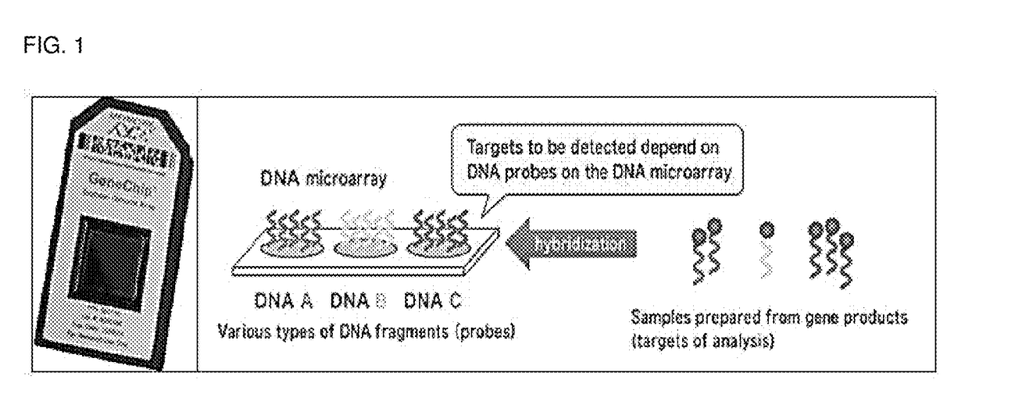
FIG. 1 shows a schematic view of a DNA microarray using an SNP chip.

Example 2: Selection of SNPs Related to the Risk of Developing Precocious Puberty As shown in FIG. 1, the extracted DNA sample was treated on a chip (axiom precision medicine research array (PMRA) microarray chip, affymetrix, Santa Clava, CA, USA) containing a total of 8,754,887 SNP probes and the SNP genotype was investigated as hybridization difference to the probe.

First, as a result of performing a quality check (QC) on the PMRA chip containing a total of 8,754,887 SNP probes, it was confirmed that the cluster was well formed, and from the call rate (98.1%) and DQC (development quality check) results, the usefulness of the PMRA chip was verified.

Figure 2:
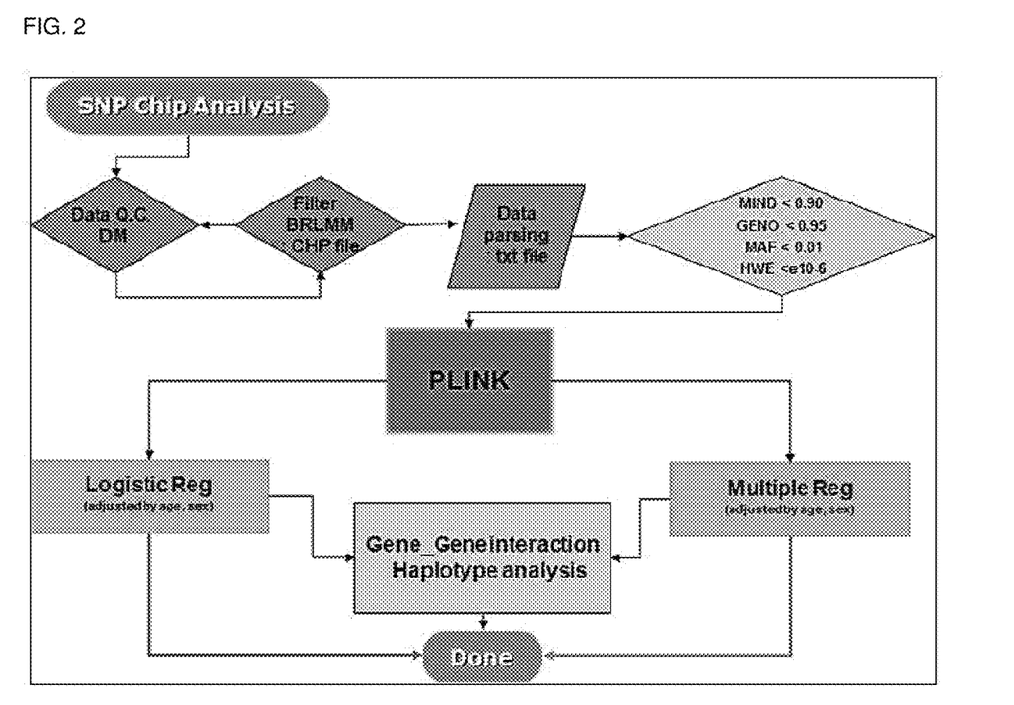
FIG. 2 shows a flowchart of GWAS analysis using a PLINK program.

Thereafter, a genome wide association study (GWAS) was performed using the SNP genotype data and clinical data of the precocious puberty test, obtained from 700 girl patients with precocious puberty and 300 normal little girls. As shown in FIG. 2, genome wide association study was performed on patients and normal persons using the PLINK program.

Figure 3:
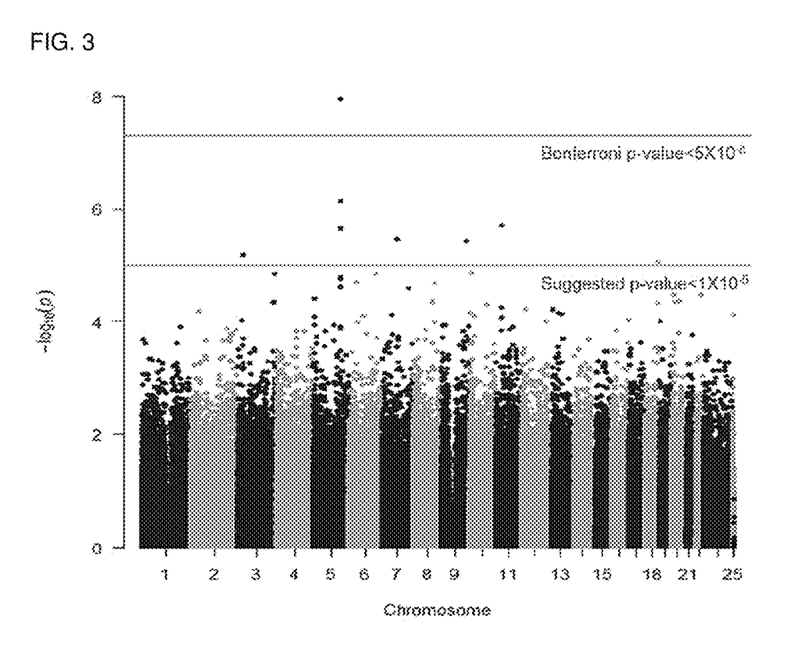
FIG. 3 shows a GWAS Manhattan plot results of precocious puberty patients and normal persons.
Figure 4:
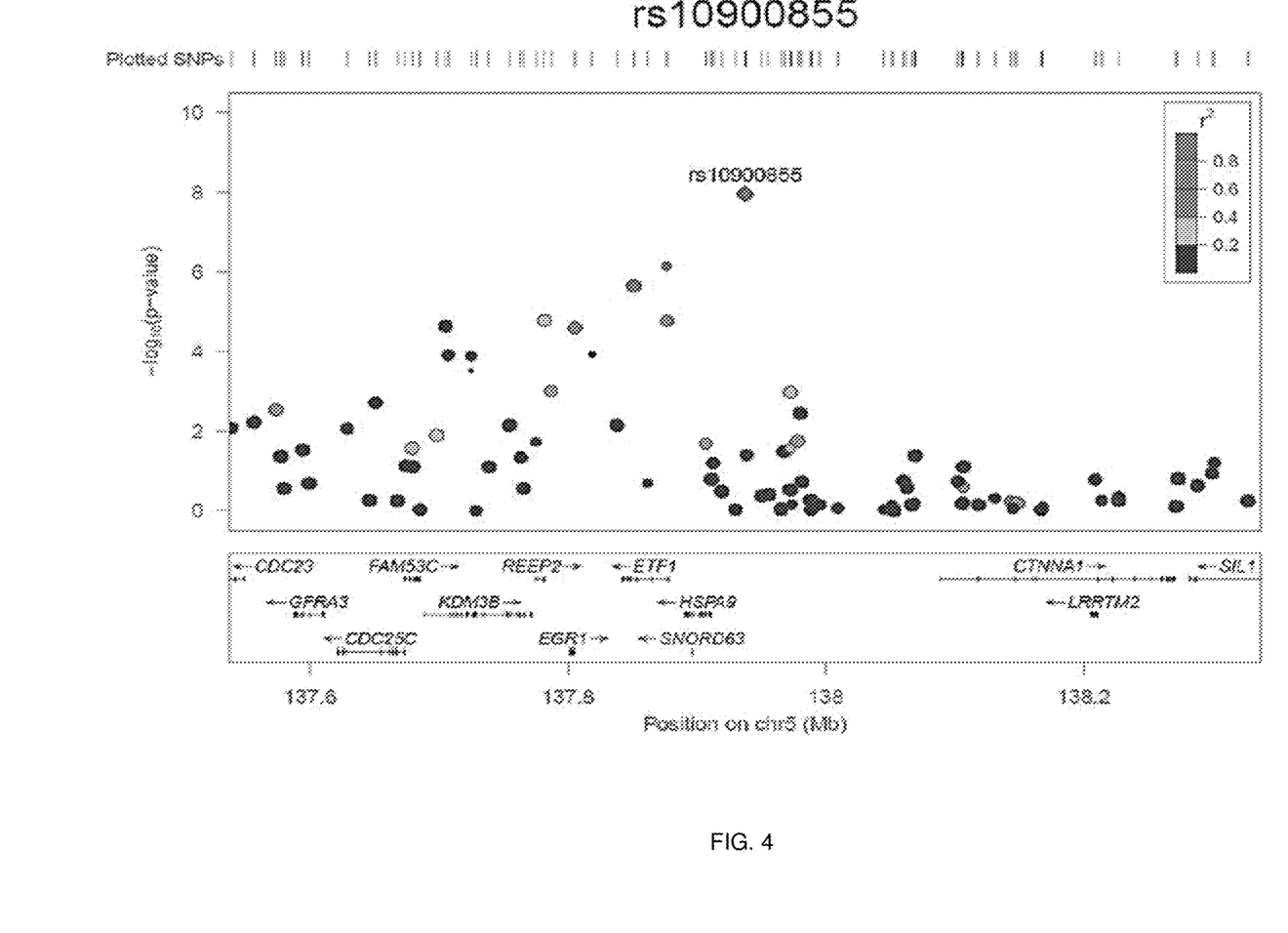
FIG. 4 shows the position of rs10900855 SNP on a chromosome.

As a result, as shown in Table 1 below and FIG. 3, 45 SNPs showing statistical significance values (p-value) for each chromosome were discovered in the GWAS Manhattan plot of little girls with precocious puberty, and it was confirmed that the following SNPs were associated with precocious puberty. In addition, as shown in FIG. 4, it was confirmed that the rs10900855 SNP on chromosome 5 showed the highest significance.

TABLE 1

| | Chromosome | SNP | Variant | NMISS | Degree of risk | Significance level | Sensitivity | Specificity | Precision | $R^2$ | Biomarker |
|---|---|---|---|---|---|---|---|---|---|---|---|
| s01 | 5 | rs1 | C | 883 | 2.21 | 1.10E−08 | 0 | 100 | 66.6 | 0.041 | SNP1 |
| s02 | 5 | rs2 | T | 872 | 2.006 | 7.07E−07 | Collinearity | | 66.6 | | |
| s03 | 11 | rs3 | T | 880 | 0.5839 | 1.94E−06 | 9.5 | 95.4 | 66.8 | 0.064 | SNP2 |
| s04 | 5 | rs4 | T | 884 | 1.959 | 2.24E−06 | Collinearity | | 66.6 | | |
| s05 | 7 | rs4 | C | 882 | 0.1212 | 3.48E−06 | 16.7 | 94.2 | 68.5 | 0.089 | SNP3 |
| s06 | 9 | rs6 | A | 875 | 2.493 | 3.66E−06 | 16.4 | 95.7 | 69.2 | 0.111 | SNP4 |
| s07 | 3 | rs7 | C | 873 | 0.4638 | 6.41E−06 | 30.6 | 91.1 | 70.8 | 0.133 | SNP5 |
| s08 | 18 | rs8 | C | 877 | 0.5933 | 8.66E−06 | 39.9 | 88.3 | 72.2 | 0.158 | SNP6 |
| s09 | 10 | rs9 | A | 884 | 0.298 | 1.39E−05 | | | 71.6 | 0.17 | |
| s10 | 3 | rs10 | G | 883 | 0.5668 | 1.43E−05 | 36.5 | 90.6 | 72.5 | 0.179 | SNP7 |
| s11 | 6 | rs11 | T | 882 | 0.4147 | 1.44E−05 | 39.9 | 89.5 | 73 | 0.192 | SNP8 |
| s12 | 5 | rs12 | T | 881 | 1.775 | 1.66E−05 | | | 72.4 | 0.192 | |
| s13 | 5 | rs13 | G | 878 | 1.844 | 1.69E−05 | 40 | 89.4 | 73 | 0.193 | SNP9 |
| s14 | 6 | rs14 | C | 874 | 0.5242 | 1.99E−05 | 47.3 | 87.4 | 74 | 0.209 | SNP10 |
| s15 | 8 | rs15 | C | 877 | 0.2951 | 2.04E−05 | 48.4 | 86.9 | 74.2 | 0.213 | SNP11 |
| s16 | 5 | rs16 | G | 882 | 1.571 | 2.39E−05 | | | 74.1 | 0.221 | |
| s17 | 5 | rs17 | G | 881 | 1.766 | 2.51E−05 | | | 74.1 | 0.213 | |
| s18 | 7 | rs18 | A | 881 | 1.648 | 2.57E−05 | 46.9 | 89.4 | 75.4 | 0.23 | SNP12 |
| s19 | 22 | rs19 | G | 882 | 0.6026 | 3.36E−05 | 54 | 87.1 | 76.2 | 0.25 | SNP13 |
| s20 | 20 | rs20 | A | 883 | 1.605 | 3.38E−05 | 52.9 | 88.9 | 77 | 0.256 | SNP14 |
| s21 | 5 | rs21 | T | 881 | 0.6326 | 3.94E−05 | 52 | 89.6 | 77.2 | 0.274 | SNP15 |
| s22 | 8 | rs22 | A | 884 | 1.533 | 4.27E−05 | | | 77.2 | 0.286 | |
| s23 | 20 | rs23 | T | 881 | 0.4467 | 4.42E−05 | | | 77.2 | 0.289 | |
| s24 | 8 | rs24 | T | 880 | 1.535 | 4.46E−05 | | | 77 | 0.285 | |
| s25 | 3 | rs25 | T | 875 | 2.006 | 4.52E−05 | 56.3 | 88 | 77.4 | 0.291 | SNP16 |
| s26 | 20 | rs26 | T | 884 | 0.5289 | 4.53E−05 | 55.9 | 89.1 | 78 | 0.3 | SNP17 |
| s27 | 18 | rs27 | T | 883 | 0.5919 | 4.68E−05 | | | 77.5 | 0.302 | |
| s28 | 10 | rs28 | C | 884 | 1.827 | 5.05E−05 | | | 77.8 | 0.314 | |
| s29 | 11 | rs29 | T | 883 | 0.6117 | 5.63E−05 | | | 77.8 | 0.301 | |
| s30 | 13 | rs30 | G | 871 | 0.5993 | 6.00E−05 | | | 76.9 | 0.301 | |
| s31 | 12 | rs31 | G | 883 | 0.5011 | 6.12E−05 | 59.8 | 88 | 78.6 | 0.31 | SNP18 |
| s32 | 2 | rs32 | 1 | 884 | 2.67 | 6.54E−05 | 60.5 | 88.1 | 79 | 0.325 | SNP19 |
| s33 | 13 | rs33 | T | 877 | 1.569 | 6.93E−05 | | | 78.6 | 0.331 | |
| s34 | 10 | rs34 | C | 883 | 0.3324 | 7.16E−05 | | | 78.9 | 0.329 | |
| s35 | 13 | rs35 | A | 878 | 0.583 | 7.35E−05 | 60.4 | 88.3 | 79.1 | 0.332 | SNP20 |
| s36 | 7 | rs36 | A | 883 | 0.654 | 7.60E−05 | | | 79.1 | 0.339 | |
| s37 | 25 | rs37 | C | 884 | 0.6517 | 7.72E−05 | 62.7 | 87.9 | 79.6 | 0.342 | SNP21 |

TABLE 1-continued

| | Chromosome | SNP | Variant | NMI SS | Degree of risk | Significance level | Sensitivity | Specificity | Precision | $R^2$ | Biomarker |
|---|---|---|---|---|---|---|---|---|---|---|---|
| s38 | 10 | rs38 | T | 883 | 0.4703 | 7.89E−05 | 65.5 | 88.1 | 80.7 | 0.358 | SNP22 |
| s39 | 6 | rs39 | G | 880 | 0.6486 | 7.95E−05 | 66 | 88.6 | 81.2 | 0.362 | SNP23 |
| s40 | 5 | rs40 | A | 871 | 0.6378 | 8.32E−05 | | | 81.2 | 0.358 | |
| s41 | 11 | rs41 | C | 883 | 1.52 | 8.36E−05 | | | 80.7 | 0.363 | |
| s42 | 16 | rs42 | G | 883 | 1.543 | 9.43E−05 | | | 81.1 | 0.372 | |
| s43 | 3 | rs43 | T | 882 | 0.3479 | 9.63E−05 | | | 81 | 0.366 | |
| s44 | 19 | rs44 | A | 881 | 0.6068 | 9.80E−05 | | | 80.3 | 0.368 | |
| s45 | 12 | rs45 | C | 879 | 2.188 | 9.88E−05 | | | 80.4 | 0.371 | |

Figure 5:
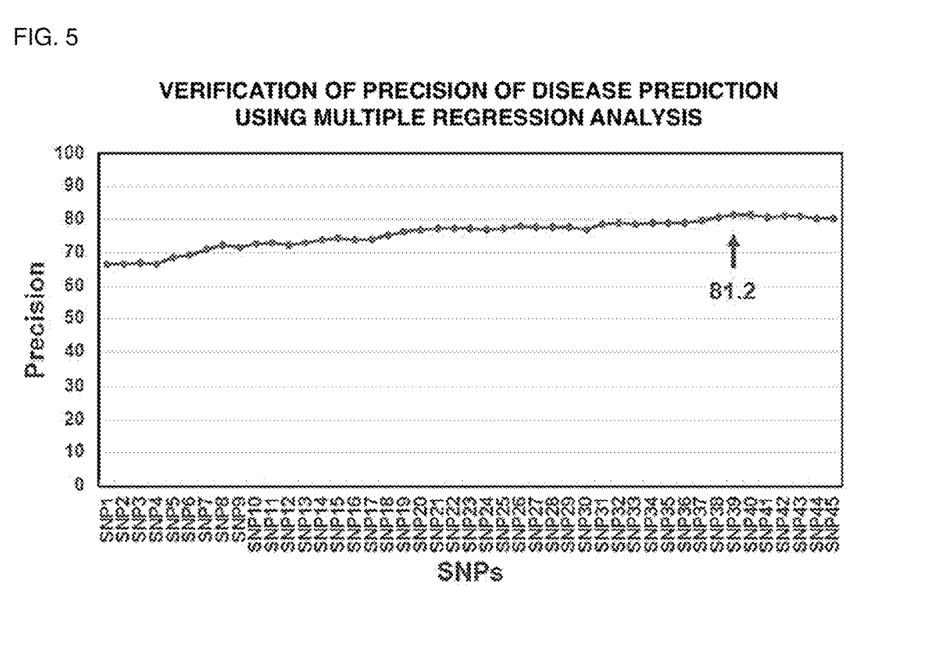
FIG. 5 shows the results of verifying precision of disease prediction using multiple regression analysis.

In addition, as shown in FIG. 5, in the multiple regression analysis of 45 SNPs, 23 SNPs were finally selected as shown in Table 2 below by analyzing the SNPs affecting the increase in the precision value. As a result of developing a precocious puberty prediction model using the following 23 SNPs and the following calculation formula, it can be seen that the prediction rate and precision of early diagnosis of precocious puberty, a multifactorial disease, are very high with a sensitivity of 66%, a specificity of 88.6%, and an precision of 81.2%.

$$\text{Formula} = 3.374 + \Sigma(i=1\sim23)[\text{SNPiB}*\text{SNPiGenotype}(0 \text{ or } 1 \text{ or } 2)] \quad \text{[Calculation Formula]}$$

(0: Major allele homozygote, 1: Heterozygote, 2: Minor allele homozygote); High risk prediction=Formula <0.

TABLE 2

| Biomarker | Single nucleotide polymorphism | Chromosome | Chromosomal location | Variant type | Degree of risk | Significance level (p-value) |
|---|---|---|---|---|---|---|
| SNP1 | rs10900855 | 5 | 137937537 | C | 2.21 | 1.1E−08 |
| SNP2 | rs373629 | 11 | 30643668 | T | 0.5839 | 1.9E−06 |
| SNP3 | rs56252016 | 7 | 78084567 | C | 0.1212 | 3.5E−06 |
| SNP4 | rs62579679 | 9 | 130141353 | A | 2.493 | 3.7E−06 |
| SNP5 | rs4680885 | 3 | 27973513 | C | 0.4638 | 6.4E−06 |
| SNP6 | rs4891764 | 18 | 67320971 | C | 0.5933 | 8.7E−06 |
| SNP7 | rs6806402 | 3 | 188237881 | G | 0.5668 | 1.4E−05 |
| SNP8 | rs17321070 | 6 | 137554245 | T | 0.4147 | 1.4E−05 |
| SNP9 | rs154069 | 5 | 137876920 | G | 1.844 | 1.7E−05 |
| SNP10 | rs35890417 | 6 | 38920449 | C | 0.5242 | 2.0E−05 |
| SNP11 | rs16882683 | 8 | 112828038 | C | 0.2951 | 2.0E−05 |
| SNP12 | rs12707194 | 7 | 134644454 | A | 1.648 | 2.6E−05 |
| SNP13 | rs11705577 | 22 | 43645133 | G | 0.6026 | 3.4E−05 |
| SNP14 | rs3903703 | 20 | 12945963 | A | 1.605 | 3.4E−05 |
| SNP15 | rs6555069 | 5 | 2182854 | T | 0.6326 | 3.9E−05 |
| SNP16 | rs9849502 | 3 | 184087417 | T | 2.006 | 4.5E−05 |
| SNP17 | rs7267229 | 20 | 20914430 | T | 0.5289 | 4.5E−05 |
| SNP18 | rs12368628 | 12 | 16128785 | G | 0.5011 | 6.1E−05 |
| SNP19 | rs72875506 | 2 | 43431337 | T | 2.67 | 6.5E−05 |
| SNP20 | rs4083786 | 13 | 71138478 | A | 0.583 | 7.3E−05 |
| SNP21 | rs5982579 | 25 | 2633801 | C | 0.6517 | 7.7E−05 |
| SNP22 | rs7070678 | 10 | 29812602 | T | 0.4703 | 7.9E−05 |
| SNP23 | rs10943068 | 6 | 73531644 | G | 0.6486 | 7.9E−05 |

That is, in the present invention, it was confirmed that a total of 23 single nucleotide polymorphisms (SNPs) including rs10900855 are closely related to the risk of developing precocious puberty. Therefore, the 23 single nucleotide polymorphisms can be usefully utilized for diagnosing precocious puberty or predicting the risk of developing the disease.

As the specific parts of the present invention have been described in detail above, for those of ordinary skill in the art, these specific descriptions are only preferred embodiments, and it is clear that the scope of the present invention is not limited thereto. Accordingly, the substantial scope of the present invention will be defined by the appended claims and their equivalents.

The scope of the present invention is indicated by the following claims, and all changed or modified forms derived from the meaning and scope of the claims and their equivalent concepts should be construed as being included in the scope of the present invention.

What is claimed is:

1. A method for preventing or treating precocious puberty in a human subject comprising:
   (a) obtaining a nucleic acid sample from the human subject;
   (b) detecting, in the nucleic acid sample, presence of one or two C alleles at SNP rs10900855 and one or two G alleles at SNP rs6806402;
   (c) identifying the human subject as having an increased risk of developing precocious puberty; and
   (d) administering a pharmaceutical composition including a therapeutically effective amount of a gonadotropin-releasing hormone agonist (GnRHa) to the human subject.

2. The method of claim 1, wherein the nucleic acid sample further comprises a polynucleotide consisting of 5-100 consecutive DNA sequences comprising one or two C alleles at SNP rs56252016.

3. The method of claim 1, wherein the GnRHa is selected from the group consisting of leuprolide, triptorelin, and salts thereof.

4. The method of claim 1, wherein the GnRHa is leuprolide acetate or triptorelin acetate.

\* \* \* \* \*